United States Patent [19]

Benner

[11] Patent Number: 5,139,942
[45] Date of Patent: Aug. 18, 1992

[54] METHOD FOR PRODUCING THE NDE I RESTRICTION ENDONUCLEASE AND METHYLASE

[75] Inventor: Jack S. Benner, Hamilton, Mass.

[73] Assignee: New England Biolabs, Inc., Beverly, Mass.

[21] Appl. No.: 196,028

[22] Filed: May 19, 1988

[51] Int. Cl.$^5$ .................. C12N 9/22; C12N 1/21; C12N 15/52

[52] U.S. Cl. .................. 435/199; 435/252.33; 435/320.1; 435/193; 536/27; 935/29; 935/73; 935/80; 935/82

[58] Field of Search .............. 435/199, 172.3, 320.1, 435/252.3; 935/29, 73, 80, 82; 536/27

[56] References Cited
FOREIGN PATENT DOCUMENTS 0193413 3/1986 European Pat. Off. .

OTHER PUBLICATIONS

Mann et al., Gene 3:97–112, 1978.
Kosykh et al., Molec. Gen. Genet. 178: 717–719, 1980.
Walder et al., Proc. Nat. Acad. Sci., USA 78: 1503–1507, 1981.
Bougueleret et al., Nucleic Acids Res. 12:3659–3676, 1984.
Gingeras & Brooks Proc. Natl. Acad. Sci. USA 80: 402–406, 1983.
Theriault & Roy Gene 19:355–359, 1982.
Blumenthal et al., J. Bacteriol 164:501–509, 1985.
Kiss et al., Nucleic Acids Res. 13:6403–6421, 1985.
Szomolanyi et al., Gene 10:219–225, 1980.
Janulaitis et al., Gene 20:197–204, 1982.
Kiss & Baldauf, Gene 21:111–119, 1983.
Walder et al., J. Biol. Chem. 258:1235–1241, 1983.
Raleigh & Wilson, Proc. Natl. Acad. Sci. USA 83: 9070–9074, 1986.
Birnborn & Doly, Nucleic Acids Res. 7:1513, 1979.
Watson, R. J. et al., (1982) Febs Lett. 150(1), 114–116.
Walder, R. Y. et al., (1984) J. Biol. Chem. 259(12), 8015–8026.
Schoner, B. et al., (1983) Gene 24, 227–236.
Newman, A. K. et al., (1981) J. Biol. Chem. 256(5), 2131–2139.
Greene, P. J. et al., (1981) J. Biol. Chem. 256(5), 2143–2153.

*Primary Examiner*—Charles L. Patterson
*Attorney, Agent, or Firm*—Gregory D. Williams; David G. Conlin

[57] ABSTRACT

The present invention is directed to a method for cloning and producing the Nde I restriction endonuclease by 1) introducing the restriction endonuclease gene from *Neisseria denitrificans* into a host whereby the restriction gene is expressed; 2) fermenting the host which contains the vector encoding and expressing the Nde I restriction endonuclease, and 3) purifying the Nde I restriction endonuclease from the fermented host which contains the vector encoding and expressing the Nde I restriction endonuclease activity.

7 Claims, 4 Drawing Sheets

Nde I Endonuclease Purification

Purified Nde I Endonuclease pNdeIRM6.7-A6

A  : BstEII Lambda DNA Standard Digest.
B C : Extracts from pNdeIRM6.7-A6 ; 1 & 5 ul.
D E : Extracts from pNdeIRM6.7-B9 ; 1 & 5 ul.
F G : Extracts from pNdeIRM6.7-A6 ; 1 & 5 ul.
H I : Extracts from pNdeIRM6.7-A6 ; 1 & 5 ul.
J K : Extracts from pNdeIRM6.7-B9 ; 1 & 5 ul.
L M : Extracts from pNdeIRM6.7-B9 ; 1 & 5 ul.
N O : Extracts from pNdeIRM6.7-A6 ; 1 & 5 ul.
P Q : Extracts from pNdeIRM6.7-A6 ; 1 & 5 ul.
R S : Extracts from pNdeIRM6.7-B9 ; 1 & 5 ul.
 T  : BstEII Lambda DNA Standard Digest.

U  : BstEII Lambda DNA Standard Digest.
V W : Extracts from RR1/pUC19 ; 1 & 5 ul.
 X  : Nde I control digest on lambda DNA.
 Y  : Lambda DNA.
 Z  : BstEII Lambda DNA Standard Digest.

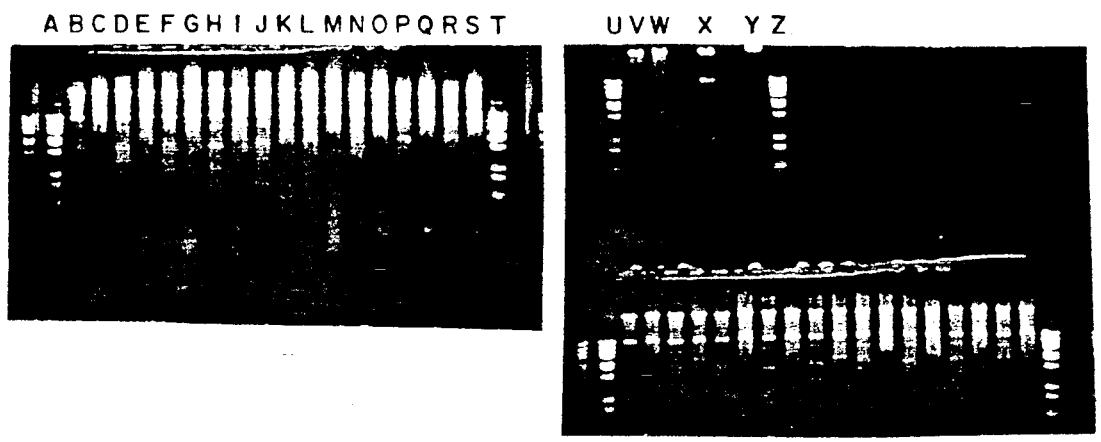

FIG. 4

A : BstEII Lambda DNA Standard Digest.
B : pNdeIRM6.7-A6 uncut.
C : pNdeIRM6.7-A6 + NdeI.
D : pNdeIRM6.7-A6 + HindIII.
E : pNdeIRM6.7-A6 + SphI.
F : pNdeIRM6.7-A6 + BsmI.
G : pNdeIRM6.7-A6 + HincII.
H : pNdeIRM6.7-A6 + AvaI.
I : pNdeIRM6.7-A6 + StyI.
J : pNdeIRM6.7-A6 + ClaI.
K : pNdeIRM6.7-A6 + KpnI.
L : pNdeIRM6.7-B9 uncut.
M : pNdeIRM6.7-B9 + NdeI.
N : pNdeIRM6.7-B9 + HindIII.
O : pNdeIRM6.7-B9 + SphI.
P : pNdeIRM6.7-B9 + BsmI.
Q : pNdeIRM6.7-B9 + HincII.
R : pNdeIRM6.7-B9 + AvaI.
S : pNdeIRM6.7-B9 + StyI.
T : pNdeIRM6.7-B9 + ClaI.

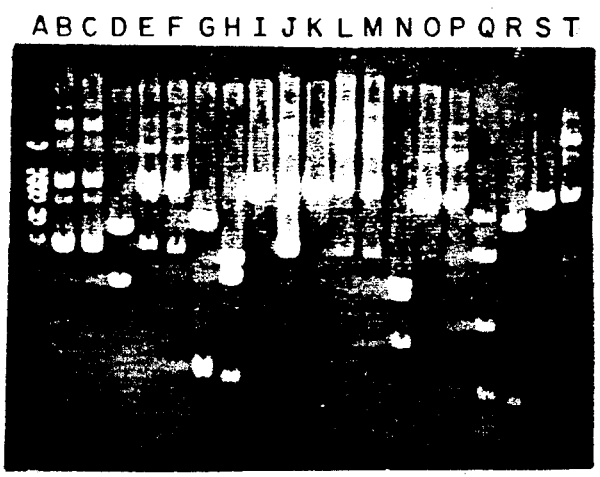

FIG. 5

METHOD FOR PRODUCING THE NDE I RESTRICTION ENDONUCLEASE AND METHYLASE

BACKGROUND OF THE INVENTION

The present invention relates to clones for the Nde I restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., *Gene* 3: 97-112, (1978); EcoRII: Kosykh et al., *Molec. gen. Genet* 178: 717-719, (1980); PstI: Walder et al., *Proc. Nat. Acad. Sci. USA* 78 1503-1507, (1981)). Since the presence of restriction-modification systems in bacteria enables them to resist infection by bacteriophages, cells that carry cloned restriction-modification genes can, in principle, be selectively isolated as survivors from libraries that have ben exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucleic Acids Res.* 12:3659-3676, (1984); PaeR7: Gingeras and Brooks, *Proc. Natl. Acad. Sci. USA* 80:402-406, (1983); Theriault and Roy, *Gene* 19:355-359, (1982); PvuII: Blumenthal et al., *J. Bacteriol.* 164:501-509, (1985)).

A third approach, and one that is being used to clone a growing number of systems, involves selecting for an active methylase gene referring to our Patent application No. 707079 and (BsuRI: Kiss et al., *Nucleic Acids Res.* 13:6403-6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219-225, (1980); BcnI: Janulaitis et al, *Gene* 20: 197-204 (1982); BsuRI: Kiss and Baldauf, *Gene* 21: 111-119, (1983); and MspI: Walder et al., *J. Biol. Chem.* 258:1235-1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E. coli* react adversely to cytosine modification; they possess systems that destroy DNA containing methylated cytosine (Raleigh and Wilson, *Proc. Natl. Acad. Sci., USA* 83:9070-9074, (1986)). Cytosine-specific methylase genes cannot be cloned easily into these strains, either on their own, or together with their corresponding endonuclease genes. To avoid this problem it is necessary to use mutant strains of *E. coli* (McrA⁻ and McrB⁻) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the Nde I restriction endonuclease and modification methylase derived from *Neisseria denitrificans*, as well as related methods for the production of the enzymes. More specifically, this invention relates to clones which express the restriction endonuclease Nde I, an enzyme which recognizes the DNA sequence CA TATG and cleaves as indicated between the first 5' A and T by the arrow. See *FEBS Letters*. 150: 114-116, (1982), the disclosure of which is hereby incorporated by reference herein.

The preferred method for cloning this enzyme comprises forming a library containing the DNA from *Neisseria denitrificans*, isolating those clones which contain DNA coding for the Nde I modification methylase and screening among these to identify those that also contain the Nde I restriction endonuclease gene.

BRIEF DESCRIPTION OF THE DRAWINGS

FIG. 4 consists of two photographs of an agarose gel demonstrating NdeI restriction endonuclease activity in cell extracts of *E. coli* RR1 (ATCC 31343) carrying pNdeIRM6.7-A6 and pNdeIRM6.7B9 on lambda DNA using 1 and 5 ul of extract.

FIG. 5 is a photograph of an agarose gel demonstrating Nde I restriction endonuclease activity in cell extracts of *E. coli* RR1 (ATCC 31343) carrying pNdeIRM6.7-A6 and pNdeIRM6.7-B9.

DETAILED DESCRIPTION OF THE INVENTION

Figure 1:
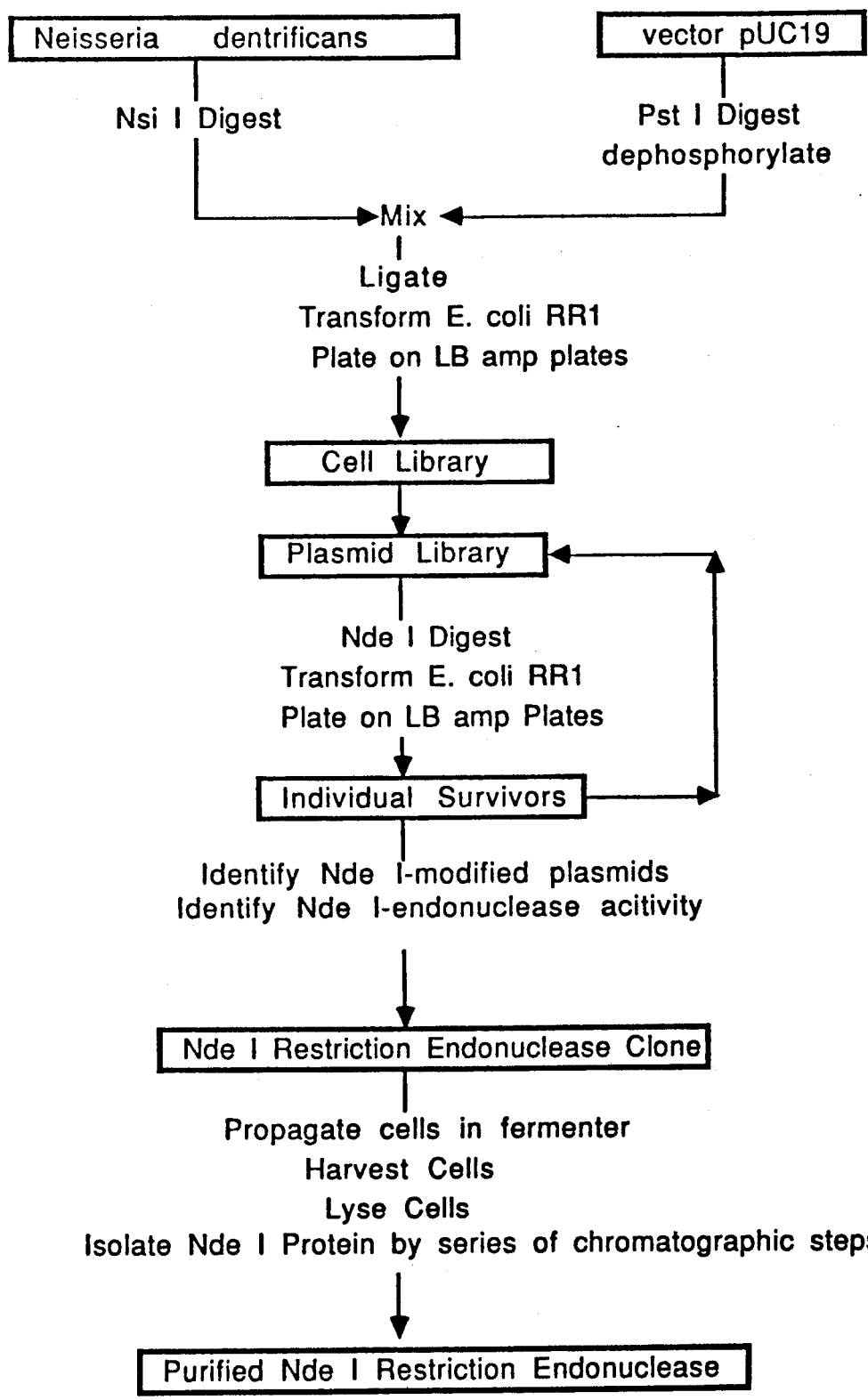
FIG. 1 illustrates the scheme for cloning the Nde I restriction endonuclease.
Figure 2:
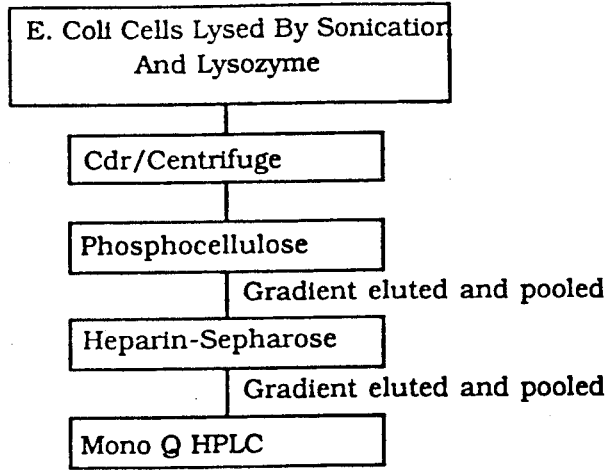
FIG. 2 illustrates the scheme for producing the Nde I restriction endonuclease.

The present invention provides a method for cloning Nde I restriction and modification genes and producing the restriction endonuclease Nde I from clones produced thereby. This approach takes advantage of the fact that clones have been selected on the basis of containing expressed Nde I restriction and methylase genes by the use of an endonuclease selection. Such clones are resistant to digestion in vitro by Nde I restriction endonuclease.

The methods described herein by which Nde I restriction gene and methylase gene are preferably cloned and expressed include the following steps:

1. The genomic DNA of Neisseria denitrificans strain is purified.

2. The genomic DNA is digested fully with a restriction endonuclease such as Nsi I restriction endonuclease.

3. The resulting Nsi I fragments are ligated into the Pst I cloning site of a cloning vector, such as pUC19 or pBR322 or the Nsi I sites of pACYC177 and the mixture is used to transform an appropriate host cell such as *E. coli* RR1 cells.

4. The transformed mixture is plated onto media selective for transformed cells, such as the antibiotic ampicillin. After incubation, the transformed colonies are collected together into a single culture, the cell library.

5. The recombinant plasmids are purified in toto from the cell library to make the plasmid library.

6. The plasmid library is digested to completion with the Nde I restriction endonuclease, prepared from *Neisseria denitrificans* by a method similar to that described in Watson et al, supra. Nde I digestion differentially destroys unmodified, non-methylase-containing, clones, increasing the relative frequency of Nde I methylase clones.

7. The digested plasmid library is subjected to agarose gel electrophoresis and the undigested supercoiled plasmid DN is excised and eluted.

8. The excised plasmid supercoiled DNA is transformed back into an appropriate host such as *E. coli* RR1, and transformants are recovered by plating onto selective media. The colonies are picked and their DNA is analyzed for the presence of the Nde I modification gene: the plasmids that they carry are purified and incubated with the Nde I restriction endonuclease to determine whether they are resistant to digestion. Total cellular DNA (chromosomal and plasmid) is also purified and incubated with the Nde I restriction endonuclease. The DNA of clones that carry the Nde I modification gene should be fully modified, and both plasmid DNA and total DNA should be substantially resistant to digestion 9. Clones carrying the Nde I restriction endonuclease are identified by preparing crude extracts of the clones which were determined to carry the Nde I methylase gene, and assaying the crude extract for Nde I restriction endonuclease activity. The level of Nde I activity in the crude cell extract is determined to be approximately 4,500,000 units per gram of cells of the clones containing pNdeIRM6.7-A6 or approximately 500,000 units per gram of cells of the clones containing, pNdeIRM6.7-B9.

10. The clone containing the recombinant plasmids pNdeIRM6.7-A6 and pNdeIRM6.7-B6 which is positive for the Nde I restriction endonuclease activity contains a single 4.0 Kb Nsi I DNA fragment inserted into the Pst I cloning site of pUC19.

Figure 3:
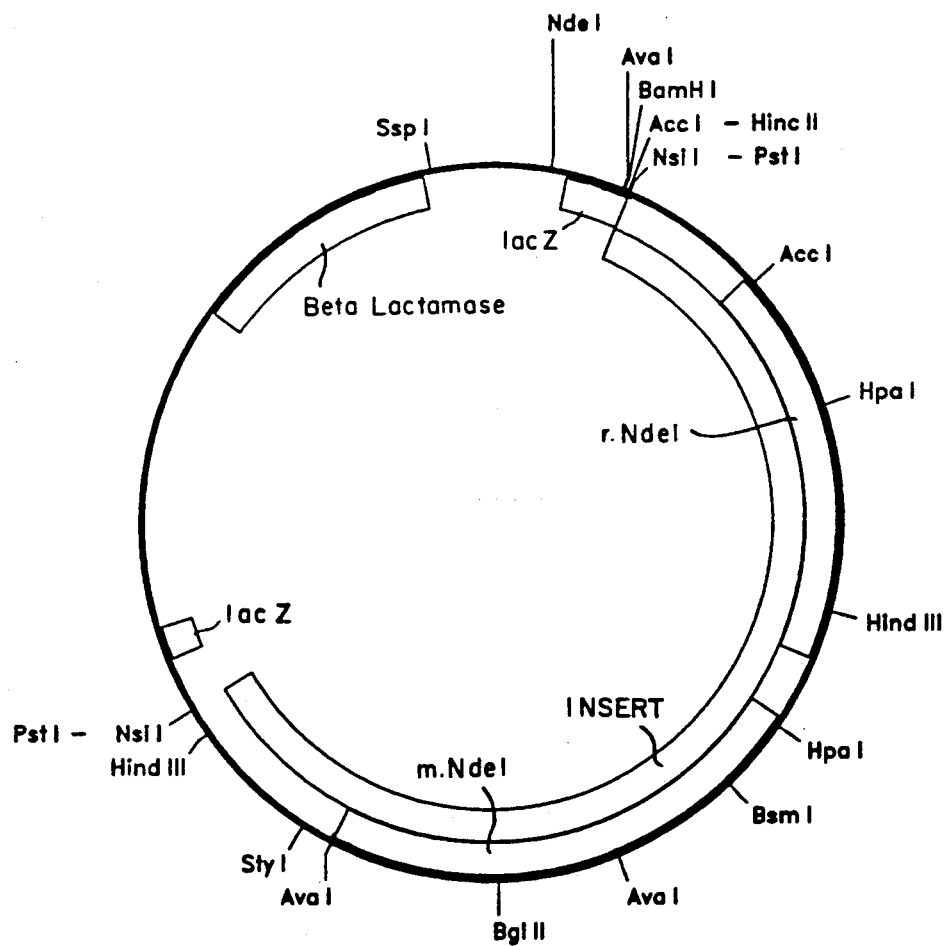
FIG. 3 is a restriction map of the 4.0 Kb Nsi I fragment from *Neisseria denitrificans* that encodes the Nde I restriction endonuclease and modification methylase in pUC19. The fragment was cloned into the PstI site of pUC19 (ATCC 37254) to create pNdeIRM6.7-A6 and pNdeIRM6.7-B9.

11. A number of restriction endonuclease sites for various restriction endonucleases were mapped on this plasmid and are shown in FIG. 3. The positions of the genes have been determined by deletion subcloning.

12. The Nde I restriction endonuclease is produced from cells carrying the Nde I restriction and modification genes on the plasmid pNdeIRM6.7-A6. The cells are propagated in a fermenter in a rich medium containing ampicillin.

13. The cells are harvested by centrifugation.

14. The cells are disrupted by sonication to produce crude cell extract containing the Nde I restriction endonuclease activity.

15. The crude cell extract containing the Nde I restriction endonuclease activity is purified by standard ion-exchange and affinity chromatography techniques.

16. The endonuclease so purified was found to be homogeneous on SDS polyacrylmide gel electrophoresis and to have a molecular weight of 43,000 daltons and a specific activity of 2,000,000 units/mg of protein titered on lambda DNA.

Although the above-outlined steps represent the preferred mode for practicing the present invention, it will be apparent to those skilled in the art that the above-described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of Nde I Restriction Endonuclease Gene

1. Genomic DNA purification: Approximately five grams of *Neisseria denitrificans* cells (NRCC 31009, NEB strain #321), were thawed and resuspended in 0.1M Tris-HCl, pH 7.1, 0.1M ETDA (25 ml) in a Corning plastic tube (50 ml). A solution of 60 mg of lysozyme in 35 ml of the above buffer was divided into two 50 ml plastic tubes and equal portions (15 ml) of the cell suspension added to each. The solutions were incubated at 37° C. for fifteen minutes. SDS was added from a 20% stock solution to adjust the final conc. of SDS to 1%. 200 ul of a Proteinase K (20 mg/ml stock) was added and incubated for one hour at 37° C. The solution appered string and diffuse at this point but was not clear. Added 2 ml of 10% SDS/8% sarcosyl to the tubes (1 ml each) and heated at 55° C. for two hours. The sample remained stringy but not totally cleared. The samples were dialyzed against TE (10 mM Tris-HCl, pH 7.1, 1 mM EDTA) (2 l) with a single change—total 16 hours. After the dialysis the solution (98 ml) was prepared for CsCl gradients by dilution with an equal vol. of TE pH 8.0, divided into two portions and to each an addition of 98.0 g of CsCl and 1 ml of a 5 mg/ml Ethidium bromide was made. The twenty tubes were spun in the Ti70 rotor for 48 hrs at 44,000 rpm. The bands were removed and extracted with water saturated isobutanol. The solution was dialyzied against the same buffer (4 l) as before and then phenol and chloroform extracted (one time each). This solution was dialyzed once again to remove phenol and then subjected to electrophoresis.

2. Limit digestion: The purified DNA was cut with Nsi I to achieve total digestion as follows: 50 ul of DNA at 100 ug/ml in 10 mM Tris pH 7.5, 10 mM MgCl$_2$, 50 mM NaCl, 10 mM mercaptoethanol buffer was dispensed into three tubes. To the tube was added 10 units of Nsi I. The tubes were incubated at 37° C. for one hour, then phenol/chloroform extracted and ethanol precipitated. The pellets were redissolved in 100 ul of 10 mM Tris-HCl, 1 mM EDTA, pH 8.0 and 10 ul from each analyzed by agarose gel electrophoresis.

3. Ligation: The fragmented DNA was ligated to pUC19 or pACYC177 as follows: 1.0 ug of Nsi I digested Neisseria denitrificans DNA (15 ul) was mixed with 0.2 ug of Nsi I-cleaved and dephosphorylated pACYC177 (2.5 ul) or with 0.2 ug of Pst I-cleaved and dephosphorylated pUC19 (2.5 ul). 2.5 ul of 10X ligation mix (500 mM Tris, pH 7.5, 100 mM MgCl$_2$, 100 mM DTT, 5 mM ATP) was added plus 2.5 ul of sterile distilled water to bring the final volume to 25 ul. 1.0 ul of T4 DNA ligase was added and the mixture allowed to incubate at 16° C. for 16 hours. Aliquiots of 2.5 and 5.0 ul were used to transform *E. coli* strain RR1 as follows: Each aliquot was mixed with 200 ul of ice-cold competent *E. coli* RR1 cells and placed on ice for thirty minutes. After a 2-minute heat shock at 42° C., the cells were diluted with one ml of Luria-broth (L-broth) and grown for one hour at 37° C.

4. Primary Cell Library: The transformed cell cultures were centrifuged, resuspended in 250 ul volumes and plated onto Luria-agar (L-agar) plates containing 100 ug/ml ampicillin or 25 ug/ml tetracycline. After overnight incubation at 37° C., the plates were removed and the approximately 5000 colonies scraped-up into 25 ml of LB with antibiotic. Plasmid DNA was prepared from these cells as follows: the cells were pelleted by centrifugation and three grams of cell paste was resuspended in 14 ml of 25 mM Tris-HCl, 10 mM EDTA pH 8.0 and 50 mM glucose. The suspension was made 1.0 mg/ml in lysozyme and incubated at 25 degrees for 5 minutes. A 27 ml aliquot of 1% sodium dodecyl sulfate and 0.2N NaOH was added followed by mixing of the solution and incubated for 5 minutes at 0 degrees. Genomic DNA was precipitated by the addition of 20 ml of ice-cold 3M potassium acetate, pH 4.8, vortexed gently for 10 seconds, left on ice for 5 minutes and centrifuged at 12,000xg for ten minutes. The supernantant was removed and extracted with an equal volume of phenol/chloroform (1:1). The layers were separated by centrifugation at 10,000xg for 5 minutes. The upper layer was removed and the nucleic acids precipitated by the addition of two volumes of ethanol. The precipitate was collected by centrifugation at 12,000xg for ten minutes. The pellet was washed with 70% ethanol once and repelleted as before. The pellet was dried under vacuum and resuspended in 8 ml of 10 mM Tris-HCl, 1 mM EDTA, pH 8.0 containing 20 ug/ml of RNAase. The DNA solution was incubated at 37 degrees for one hour and then prepared for cesium chloride-ethidium bromide equilibrium density centrifugation by the addition of 8.8 grams of cesium chloride and 0.4 ml of a solution of ethidium bromide (5 mg/ml) were added. The DNA solution was centrifuged at 44,000 rpm for 48 hours and the resulting plasmid band of DNA was removed with a syringe and 18g needle. The ethidium bromide was removed by extracting with an equal volume of CsCl-water-saturated isopropanol. The cesium chloride was removed by dialysis. The DNA was extracted with an equal volume of phenol/chloroform (1:1), extracted with an equal volume of chloroform, and subjected to dialysis.

5. Primary Selection and Selected Library: 1 ug (2.5 ul) of the plasmid library was diluted into 50 ul of restriction endonuclease digestion buffer (10 mM Tris pH 7.5, 10 mM MgCl$_2$, 10 mM mercaptoethanol, 150 mM NaCl and 100ug of bovine serum albumin). 8 units (1 ul) of Nde I restriction endonuclease were added and the tube was incubated at 37° C. for 2 hr. This reaction was mixed with 200 ul of ice-cold competent *E. coli* RR1 cells and transformed, plated and grown overnight as for the primary library. Plasmid DNA was prepared as described before for the primary library.

6. Secondary Selection: Two identical reactions of plasmid DNA from the once selected primary library were subjected to a second selection as described above. However, after one hour at 37° C. 1 units (1 ul) of Lambda exonuclease was added to one reaction and 100 units (1 ul) of exonuclease III was added to the other reaction and the two reactions were maintained at 37° C. for an additional one hour.

7. Gel Electrophoresis and Transformation: The reactions from above subjected to electrophoresis on a 0.7% agarose gel for two hours and the supercoiled plasmid DNA bands remaining intact from the digestions were excised with a razor blade while visualizing with long wave UV and placed in 1.5 ml microfue tube. 100 ul of TE (10 mM Tris-HCl, 1 mM EDTA, pH 8.0) was added and vortexed. The tube was frozen in a dry ice ethanol bath for five minutes and then thawed. Using a 200 ul pipetman tip which has been sealed in a flame the gel fragment was squished. The above freeze-thaw-squish steps were repeated twice more. The tubes were then spun in a Eppendorf microfuge at 12,000xg for 10 minutes. Approximately 125 ul of supernantant was removed. Aliquiots of 2.5 and 5.0 ul were used to transform *E. coli* strain RR1 as follows: Each aliquot was mixed with 200 ul of ice-cold competent *E. coli* RR1 cells and placed on ice for thirty minutes. After a 2-minute heat shock at 42° C., the cells were diluted with one ml of Luria-broth (L-broth) and grown for one hour at 37° C. This mixture was then subjected to centrifugation and the pelleted cells were spread on LB plates containing 8. Analysis of individuals: Thirty-eight colonies obtained from the above transformation were grown up in 10 ml cultures and the plasmids that they carried were prepared by the following miniprep purification procedure, adapted from the method of Birnboim and Doly (Nucleic Acids Res. 7: 1513 (1979)).

Miniprep Procedure: Each culture was processed as follows: The 1.5 ml overnight culture was pelleted at 6,000xg for 2 minutes. The supernatant was poured off and the cell pellet was resuspended in 150 ul of 25 mM Tris, 10 mM EDTA, 50 mM glucose, pH 8.0, containing 1 mg/ml lysozyme. After five minutes at room temperature, 200 ul of 0.2M NaOH, 1% SDS was added and the tube was shaken to lyse the cells, then placed on ice. After five minutes, 150 ul of 3M sodium acetate, pH 4.8, was added and shaken and placed on ice for an additional five minutes. The precipitate that formed was spun down at 12,000xg, 4° C. for 10 minutes. The supernantant was removed and extracted with an equal volume of phenol/chloroform (1:1). The layers were separated by centrifugation at 10,000xg for five minutes. The supernatant was poured into a centrifuge tube containing 880 ul of ethanol and mixed. After 10 minutes at room temperature, the tube was spun at 12,000xg for 10 minutes to pellet the precipitated nucleic acids. The supernatant was discarded and the pellet was washed again with one ml of 70% ethanol-water, repelleted and dried at room temperature for 30 minutes under vacuum. Once dry, the pellet was resuspended in 50 ul of 10 mM Tris, 1 mM EDTA, pH 8.0 containing 20 ug/ml RNase and incubated for 1 hour at 37° C. to digest the RNA.

The plasmid minipreps were subsequently analyzed by digestion with Nde I and Hind III.

9. Methylase Gene Clones: Many of the plasmids that were analyzed were found to carry random Nsi I fragments of DNA and to be sensitive to digestion by Nde I or to be small deletions of pUC19. These plasmids were spurious survivors of no further interest. The remaining plasmids, however, were found to be both resistant to Nde I and to carry Nsi I fragments of approximately 4.0 Kb in length. These plasmids were subsequently shown to carry both the Nde I modification methylase and restriction endonuclease genes.

10. Restriction Gene Clones: The clones identified above (section 8) as carrying the Nde I modification methylase gene were also tested for the Nde I restriction endonuclease gene. This was performed as follows: The remaining portion of the overnight culture was used to check for endonuclease activity. This was done as follows:

Endonuclease Assays:

10X restriction endonuclease buffer: 100 mM Tris, pH 7.5, 100 mM $MgCl_2$, 100 mM 2-mercaptoethanol, 500 mM NaCl.

Cell extracts were prepared as follows: Cells from one ml were pelleted by centrifugation at 4,000 rpm for five minutes. The supernatant was discarded and the pellet was resuspended in one ml of sonication buffer (10 mM Tris, pH 7.5, 100 mM NaCl, 10 mM mercaptoethanol, 1 mM EDTA) containing one mg/ml lysozyme. The suspension was swirled and left on ice for thirty minutes. A one ml sample was transferred to an Eppendorf tube and sonicated gently for two 10-second bursts to disrupt the cells. The tube was spun for five minutes in a microfuge and the supernatant was used as the cell extract. The extract, 1 ul and 5 ul, were incubated with one ug of lambda DNA in 50 ul of 1X restriction endonuclease buffer for five minutes at 37 degrees. Eighteen colonies were found to stably carry the Nde I restriction system.

All methylase positive clones were found to contain endonuclease. These clones were found to synthesize about 4,500,000 units of Nde I restriction endonuclease per gram of wet cell paste in oreintaion A and 500,000 units of Nde I restriction endonuclease per gram of wet cell paste in oreintaion B.

11. The recombinant plasmid pNdeIRM6.7-A6 which carries the genes encoding the Nde I restriction endonuclease and methylase was transferred to *E. coli* strain RR1 by transformation. A sample of pNdeIRM6.7-A6 was deposited with the American Type Culture Collection on Oct. 7, 1991 under ATCC Accession No. 75120.

12. Nde I endonuclease from *E. coli*: *E. coli* RR1/pNdeIRM6.7–A6 was propagated in a fermenter at 37 degrees C in L Broth medium consisting of: 10 grams per liter, casein hydrolysate; 5 grams per liter, yeast extract; 10 grams per liter, NaCl; 1 gram per liter, magnesium chloride-hexahydrate; 1 gram per liter, glucose; 100 mg per liter ampicillin. The pH is adjusted to 7.2 with NaOH. The cells are collected by centrifugation and the cell paste is used fresh or stored at −70° C.

13. All subsequent steps are carried out at 4° C.

14. The cell paste (24 grams) is thawed and the cells are resuspended in 100 mls sonication buffer (25 mM Tris-HCl, pH 8.0, 100 mM NaCl, 10 mM 2-mercaptoethanol and 10 mM EDTA.

15. The cells are disrupted by sonication (250 watts for two minutes, cooled on ice for five minutes, three times), to achieve release of approximately 50 mg of soluble protein per ml of suspended cells.

16. The insoluble cell debris is removed by centrifugation at 21,000×g for 20 minutes.

17. The supernatant fluid applied to phosphocellulose column (5×35 cm) (Whatman P-11) equilibrated with 20 mM KH2PO4, pH 6.9, 100 mM NaCl, and 10 mM 2-mercaptoethanol. The column is washed with two column volumes of the above buffer. The flow-though from the column is collected in a single flask. Nde I endonuclease is retained by the column and elutes between 0.3 and 0.5M NaCl. The most active fractions are pooled and dialyzed against 20 mM Tris-HCl, pH 7.4, 50 mM NaCl, and 10 mM 2-mercaptoethanol.

18. The pool from the phosphocellulose column is applied to a Heparin-Sepharose CL-6B column (2.5×25 cm) equilibrated with 20 mM Tris-HCl, pH 7.4, 50 mM NaCl, and 10 mM 2-mercaptoethanol and washed with two column volumes of the same buffer. A linear gradient of NaCl from 0.1M to 1.0M (total volume 700 ml) is developed and applied to the column. Ten ml fractions are collected. The fractions are assayed for the presence of the Nde I restriction endonuclease activity on lambda DNA. The active fractions are pooled and dialysed against 100 volumes of buffer (50 mM KCl; 20 mM Tris-HCl, pH 7.4; 10 mM 2-mercaptoethanol.

19. The dialyzed pool (50 ml) of Nde I activity is applied to a 1 ml Mono-Q FPLC column (Pharmacia) and washed with buffer Q (0.020M Tris-HCl, pH 7.4, 50 mM KCl, 10 mM 2-mercaptoethanol) and a 40 ml linear gradient from 50 mM KCl to 0.6M KCl is developed in Q buffer and applied to the column. One ml fractions are collected and assayed for the presence of Nde I restriction endonuclease activity. The two most active fractions are homogeneous.

What is claimed is:

1. Isolated DNA coding for the NdeI restriction endonuclease, wherein the isolated DNA is obtainable from the vector pNdeIRM6.7-A6.

2. A recombinant DNA vector comprising a vector into which a DNA segment coding for the NdeI restriction endonuclease has been inserted.

3. Isolated DNA coding for the NdeI restriction endonuclease and methylase, wherein the isolated DNA is obtainable from the vector pNdeIRM6.7-A6.

4. A cloning vector which comprises the isolated DNA of claim 3.

5. The cloning vector of claim 4, wherein the cloning vector comprises pNdeIRM6.7-A6.

6. A host cell transformed by the cloning vector of claims 2, 4 or 5.

7. A method of producing an NdeI restriction endonuclease comprising culturing a host cell transformed with the vector of claims 2, 4 or 5 under conditions suitable for expression of said endonuclease.

* * * * *